United States Patent [19]

Anderson et al.

[11] Patent Number: 4,930,519

[45] Date of Patent: Jun. 5, 1990

[54] METHOD OF GRAPHING CARDIOPULMONARY DATA

[75] Inventors: Catherine A. Anderson, Stillwater; Jay O. Millerhagen, Little Canada, both of Minn.

[73] Assignee: Medical Graphics Corporation, St. Paul, Minn.

[21] Appl. No.: 774,222

[22] Filed: Sep. 9, 1985

Related U.S. Application Data

[63] Continuation of Ser. No. 596,046, Apr. 2, 1984, abandoned.

[51] Int. Cl.⁵ .................................. A61B 5/205
[52] U.S. Cl. .................................. 128/671; 128/719
[58] Field of Search .................. 128/670–671, 128/699–700, 703, 719, 707; 33/1 B, 1 C; 272/69

[56] References Cited

U.S. PATENT DOCUMENTS

| | | | |
|---|---|---|---|
| 2,714,380 | 8/1955 | Freshman | 128/699 |
| 3,364,476 | 1/1968 | Kahn | 128/719 X |
| 3,675,640 | 7/1972 | Gatts | 272/69 X |
| 3,811,040 | 5/1974 | Weinfurt et al. | 128/699 X |
| 3,818,901 | 6/1974 | Sanctuary et al. | 128/719 |
| 4,112,928 | 9/1978 | Putsch | 128/707 |
| 4,282,655 | 8/1981 | Tinman | 33/1 C |
| 4,463,764 | 8/1984 | Anderson et al. | 128/671 X |
| 4,550,502 | 11/1985 | Grayzel | 33/1 B |
| 4,566,461 | 1/1986 | Lubell et al. | 128/707 X |

FOREIGN PATENT DOCUMENTS 1123404  9/1956  France ........................ 128/670

*Primary Examiner*—Angela D. Sykes
*Attorney, Agent, or Firm*—Orrin M. Haugen; Thomas J. Nikolai

[57] ABSTRACT

A method of graphically displaying cardiopulmonary function data by providing a plurality of axes radially projecting from a common point of origin, there being one such axis for each cardiopulmonary parameter to be plotted, each axis having scale markings thereon whereby the normal value for each parameter will lie an equal distance from said point of origin, and straight line segments connected between said normal values on adjacent axes will form a generally regular polygon. The cardiopulmonary function data to be displayed are then plotted on the same appropriate axis and to the same scale such that deviations of any such data from normal will result in an irregular polygon when the segments are joined between plotted values on adjacent axis. Deviations of the irregular polygon from the regular polygon thus provides a clinician with a readily visible display of possible cardiopulmonary disfunction.

5 Claims, 4 Drawing Sheets

METHOD OF GRAPHING CARDIOPULMONARY DATA

This is a continuation of application Ser. No. 596,046, filed April 2, 1984, now abandoned.

BACKGROUND OF THE INVENTION

This invention relates generally to a method for displaying numerical data obtained from physical measurements, and more specifically to a new method of presenting graphic data pertaining to cardiopulmonary function data obtained during the course of exercise testing on living subjects whereby the measurements indicative of abnormal values will be readily apparent.

In co-pending Anderson et al. application for U.S. Pat. No. 306,607 filed September 29, 1981, there is described a cardiopulmonary exercise system which allows for real-time, breath-by-breath acquisition, analysis, display and printing of an individual's physiologic parameters which are measured during the course of an exercise regimen. That application describes in detail the hardware and software implementation of the exercise system whereby a wide variety of measurements may be taken and used in computing numerous cardiopulmonary parameters which are deemed of interest to trained medical personnel in evaluating the metabolic state of the subject under test. Basically, that system measures and/or computes data that are ultimately stored in a memory but which may be printed out in tabular form or, alternatively, may be displayed on conventional Cartesian coordinates where one parameter is chosen to be the independent variable and another parameter is chosen to be the dependent variable.

It has been found that the tabular presentation of numerical data does not lend itself to rapid analysis for the purpose of detecting cardiopulmonary abnormalities. While highly experienced medical personnel are able to interpret such data, it has been found that by appropriating presenting it in a graphical form, recognition of disease conditions and/or the ability to diagnose cardiopulmonary disfunction is enhanced.

SUMMARY OF THE INVENTION

In accordance with the teachings of the present invention, cardiopulmonary function data can be acquired during the course of an exercise regimen using the system described in the aforereferenced Anderson, et al paternt application or any other suitable gas exchange system. Typically, that data would be stored in the memory of the host computer. Rather than merely feeding the data to an alpha/numeric printer, it is instead plotted on a planar sheet or on the face of a CRT, but in a way which facilitates recognition of deviations of the measured data from expected normal values thereof. Specifically, a plot is made of a plurality of axes, each axis comprising a straight line radiating from a point of common origin, the axes being regularly spaced from one another. For the example, and with reference to FIG. 6 of the aforereferenced Anderson, et al patent application, it may be desired to plot eight separate cardiopulmonary parameters, such as the ventilatory equivalent ($\dot{V}_E$), True $CO_2$, $CO_2$ takeup ($\dot{V}CO_2$), $O_2$ Pulse, Heart Rate, Work Rate, oxygen output ($\dot{V}O_2$), and True $O_2$. Each of these parameters is displayed in its normal units but the scales on each of the axes are arranged such that normal or expected values of each of the parameters would be displaced radially outward from the origin by an equal distance such that when the normal or expected values on adjacent axes are connected by straight line segments, a generally regular polygon results.

Once the plural axes as so scaled are developed, the actual readings obtained during the course of the exercise testing as stored in the memory are plotted on the appropriate axes and a straight line segment is made to join the actual readings on adjacent axes. If the measured parameters are abnormal, the resulting figure so generated will be an irregular polygon. By noting the shape of the irregular polygon with respect to the regular polygon, the type of disfunction existing in the subject on whom the measurements have been taken become readily apparent. The closer the actual data comes to creating a regular polygon, the closer is the subject's metabolic data to the norm.

As a further feature of the present invention, it is contemplated that the "work" parameter can be the independent variable and individual plots presented on the axes as a function of work rate. In this regard, it may be found convenient to scale each of the parameter axes such that the maximum expected value for all parameters will lie an equal distance from the center or origin. Again, by noting the extent to which the actual measured data deviates from the expected maximum, important information concerning the health state of the patient can be inferred.

OBJECTS

It is accordingly a principal object of the present invention to provide a new and improved method for displaying cardiopulmonary function data.

Another object of the invention is to provide a method for displaying cardiopulmonary function data obtained during the course of an exercise test such that any deviations of the parameters being measured from normal become noticeable.

Yet another object of the invention is to provide a method for presenting numerical data obtained during the course of a cardiopulmonary stress test so that actual measured values can be readily compared to expected values for the purpose of noting any radical deviations of the parameters from the norm.

These and other objects and advantages of the invention will become apparent to those skilled in the art from the following detailed description of a preferred embodiment, especially when considered in conjunction with the accompanying drawings.

DESCRIPTION OF THE PREFERRED EMBODIMENT

Figure 1:
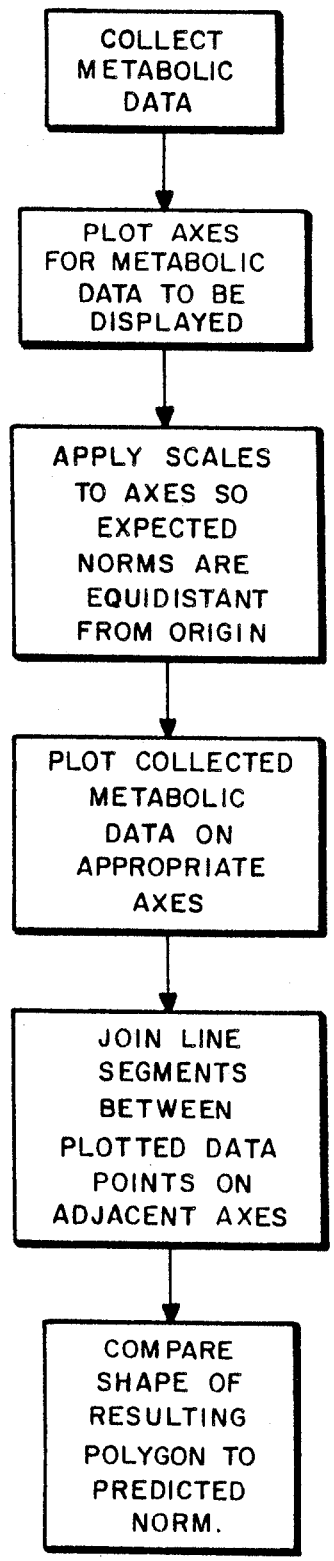
FIG. 1 illustrates a typical layout of the axes on which cardiopulmonary test data is to be plotted.

During exercise, both the ventilatory and cardiovascular systems of animals are stressed and the ability of the body to respond to this stress provides a measure of its physiological well being. In an overall evaluation of the pulmonary and cardiovascular systems, exercise testing has proved useful in establishing the degree of disability or impairment and to determine the effectiveness of treatment or rehabilitation efforts.

With respect to the cardiovascular response to exercise, at the start of the exercise period, measurements show that the heart rate and stroke volume of the heart increase to provide a rapid increase in cardiac output. Following the initial increase, the heart rate continues to rise, depending upon the work intensity, while the stroke volume tends to remain fairly well fixed. Also, at the onset of exercise where the work rate remains below the anaerobic threshold, ventilation ($\dot{V}_E$) remains quite linearly related to both oxygen uptake and carbon dioxide production ($\dot{V}O_2$ and $\dot{V}CO_2$) with carbon dioxide production being roughly a mirror image of the oxygen consumption. That is, as oxygen is burned by the active tissues, carbon dioxide is produced and as oxygen is withdrawn from the lung gases, carbon dioxide is released. For heavy and more severe work intensities, ventilation increases disportionately relative to $\dot{V}O_2$ and $\dot{V}CO_2$, the disparity representing compensation for metabolic acidosis.

By taking various measurements and/or by computing various parameters based upon such measurements, it is possible for a trained person to evaluate dyspnea, cardiopulmonary impairment and the like. Such testing is also useful in differentiating the cause of the dyspnea, e.g., when due to diffusion limitations, airway obstruction, cardiovascular insufficiency, neuromuscular and metabolic disorders and anxiety or hyperventilation states.

In the aforereferenced Anderson et al application which is assigned to the assignee of the instant application, there is described a cardiopulmonary exercise system having means for obtaining and/or calculating predetermined respiratory variables, on a breath-by-breath basis, and for storing the resulting information in the memory of a computer. More particularly, that application indicates that the system described and claimed therein is capable of accessing, computing, and storing 22 different cardiopulmonary parameters which values can be read from the computer memory and use in conjunction with a cathode ray tube type display or a hard copy printer to produce graphic presentation. Included among the parameters capable of being displayed are work rate, heart rate, $O_2$ Pulse, carbon dioxide production ($\dot{V}CO_2$), True $CO_2$ which is the $CO_2$ production divided by minute ventilation ($\dot{V}_E$), the minute ventilation itself, True $O_2$ which is the oxygen consumption divided by minute ventilation ($\dot{V}O_2/\dot{V}_E$) and the oxygen consumption itself.

In accordance with the prior art, such parameters are most commonly displayed either in the form of tabular numerical data or on standard Cartesian coordinates where a dependent variable is plotted as a function of the corresponding independent variable. While to the trained eye, such tabular data and plots can be interpreted, in accordance with the present invention, that task is simplified by a display method which tends to magnify or highlight deviations of actual measured parameters from the norm.

Referring to FIG. 1, there is illustrated by means of a block diagram a flow chart illustrating the method of the present invention. It involves first the collecting of the metabolic data to be displayed. In this regard, the data in question can be secured from the system described in the aforereferenced Anderson et al application, and following the data processing functions explained in detail therein, the parameters mentioned are stored in the memory of the host computer at addressable storage locations for later retrieval and display, either on a CRT screen or by means of a printer/plotter mechanism of known construction.

Figure 2:
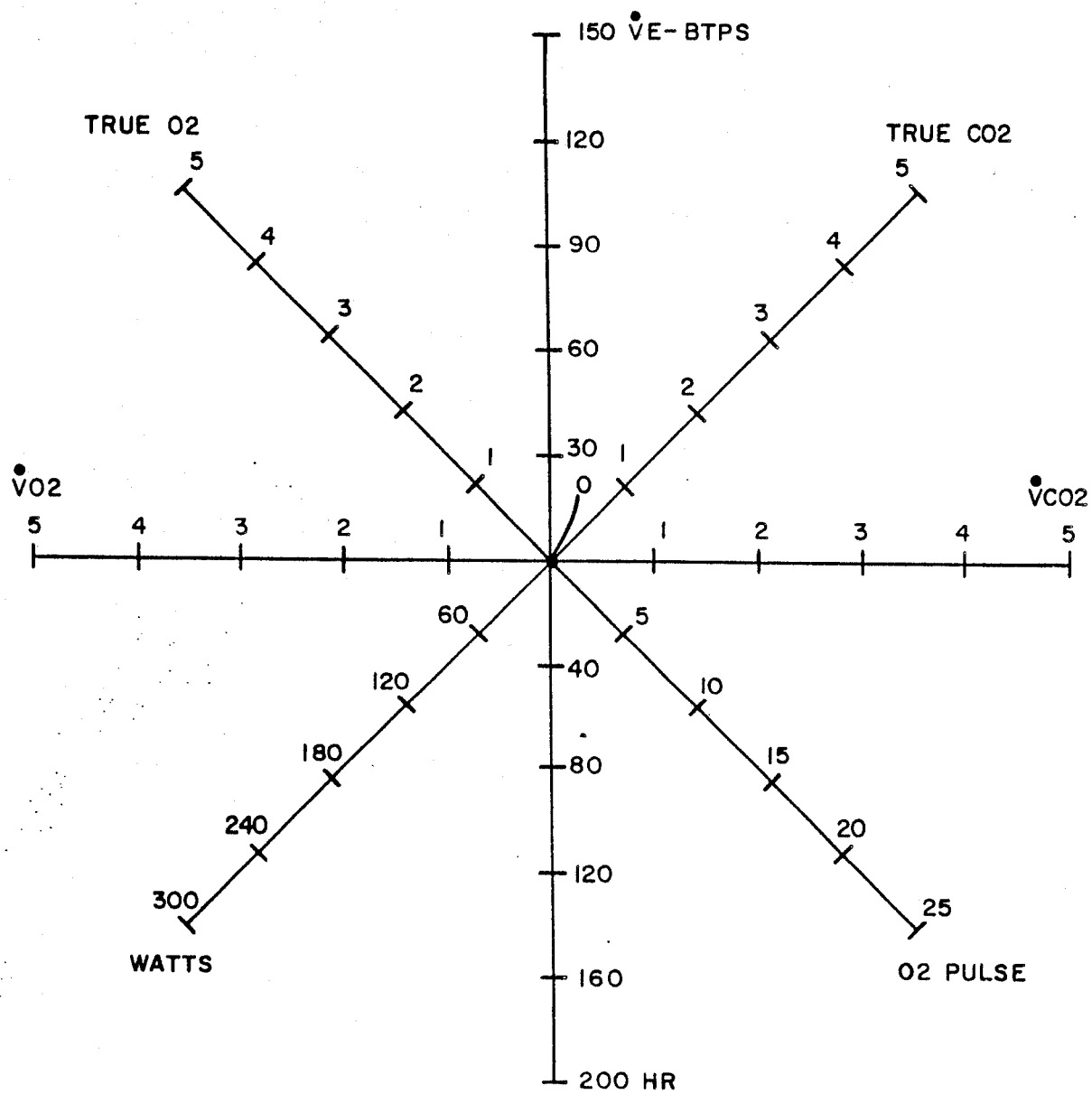
FIG. 2 illustrates a typical plot for an individual having normal cardiopulmonary metabolism.

Next, a plot is made of the axes on which desired metabolic parameters are to be displayed. FIG. 2 illustrates a typical plot of such axes where it is desired to plot eight cardiopulmonary parameters. As can be seen, the axes have a common origin, O, and extending radially outwardly therefrom at equal angular spacings are a plurality of axes, each of which is provided with a label indicating the metabolic parameter to be plotted therealong.

With due attention being paid to the range in which each of these parameters is expected to fall, appropriate scales are next applied to the axes in such a fashion that expected norms for each such parameter will be located radially outward from the origin by an equal distance.

With continued reference to the flow diagram of FIG. 1, once the axes have been laid out and appropriately scaled, the collected metabolic data stored in the computer memory or elsewhere are plotted on the appropriate axes. That is to say, the actual measured value or values of heart rate for differing levels of work are plotted on the axes labeled "HR" with the corresponding work levels being plotted on the axis labeled "WATTS". Similarly, $O_2$ Pulse, $\dot{V}CO_2$, and the other values mentioned above are plotted on the axes so labeled. Next, and with particular reference being made to FIG. 3, line segments are joined between plotted data points on adjacent axes. The polygon indicated in FIG. 3 by the broken line pattern "B" represents a first set of measurements associated with a first level of work (approximately 88 Watts) where the subject's heart rate was found to be 140 beats per minute, his $O_2$ Pulse being approximately 13 milliliters per beat, his $CO_2$ production being approximately 1.5 liters per minute, the True $CO_2$ being 4.5%, his minute ventilation being about 85 L/minute, the True $O_2$ being about 4.6% and the oxygen uptake being about 2.8 liters per minute. When these points on adjacent axes are connected by straight line segments the irregular polygon "B" results.

The solid line polygon identified by the letter C reflects the metabolic data obtained on the same patient, but at a later time after his level of work on a cycle ergometer or treadmill had been increased to the point where the subject was producing approximately 210 Watts. The corresponding values of the plotted metabolic parameters are as follows:

Heart Rate (HR) = 175 bpm
$O_2$ Pulse = 21 ml/beat
$\dot{V}CO_2$ = 3.8 L/min.
True $O_2$ = 3.7%
$\dot{V}_E$ = 128 L/min.
True $CO_2$ = 3.8%
$\dot{V}O_2$ = 3.8 L/min.

As mentioned previously, a regular polygon identified by letter A may be drawn on the same set of axes with the respective vertexes of the regular polygon being located at the normal or expected values of that parameter, assuming a healthy cardiopulmonary system. Then, the degree to which the actual measurements, e.g., polygon "C", corresponds to that regular polygon at a maximum work effort provides a readily apparent indication of the degree to which the actual measurements correspond to the norm.

Figure 3:
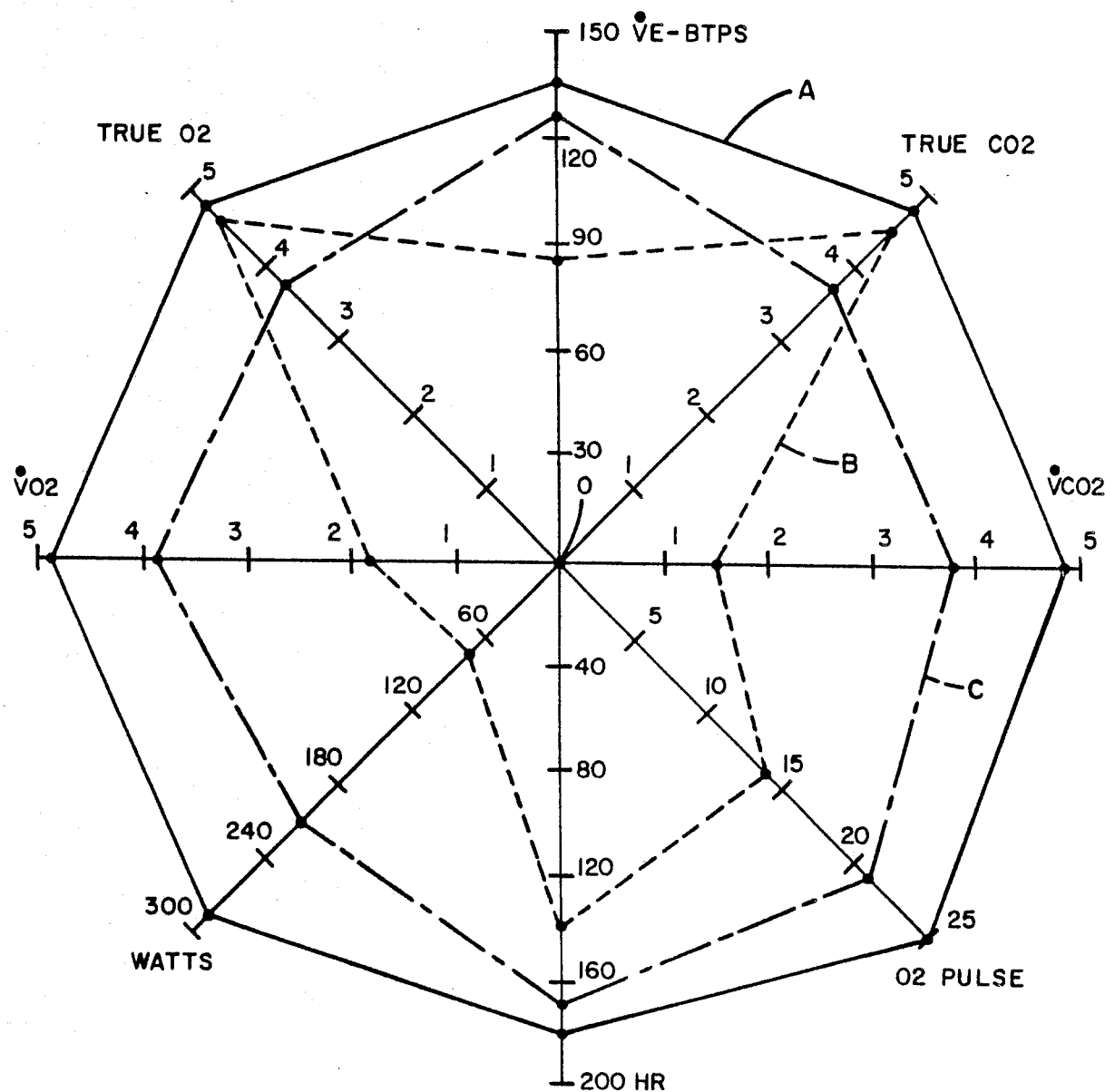
FIGS. 3 and 4 are plots of cardiopulmonary function data from two individuals suffering from one or more cardiopulmonary abnormalities.

The data used in plotting the polygon C in FIG. 3 were obtained from an athleic male, age 27, weighing 188 pounds, and being 70.5 inches (179 centimeters) tall and exhibiting good cardiopulmonary function.

The graphical representation of the subject invention also provides a ready indication of a subject's anaerobic threshold. The anaerobic threshold may be defined as the oxygen consumption ($\dot{V}O_2$) above which a sustained lactic acidosis occurs is a measure of the ability of the subject to perform endurance work. True $O_2$ and True $CO_2$ measurements may be used to determine the anaerobic threshold. Most commonly, in determining anaerobic threshold, the oxygen ventilatory equivalent is the parameter referred to. This is the ratio of minute ventilation and $O_2$ consumption ($\dot{V}_E/\dot{V}O_2$). The lowest ventilatory equivalent is defined as the anaerobic threshold. Hence, since the inverse of ventilatory equivalent is True $O_2$, it is the highest true $O_2$ value that corresponds to the anaerobic threshold and one may locate that threshold by extending a line from the maximum point on the True $O_2$ axis back to its corresponding reading on the $\dot{V}O_2$ axis. In a similar fashion, the maximum True $CO_2$ point can be extrapolated down to the $\dot{V}O_2$ axis to determine respiratory compensation. By locating the maximum value of True $O_2$ on the plot and noting the corresponding oxygen uptake for the work level producing the peak True $O_2$, the threshold is located.

Referring to the graph of FIG. 3, it can be seen that the subject in question demonstrates an anaerobic threshold occurring at approximately 50% of maximum $\dot{V}O_2$.

Figure 4:
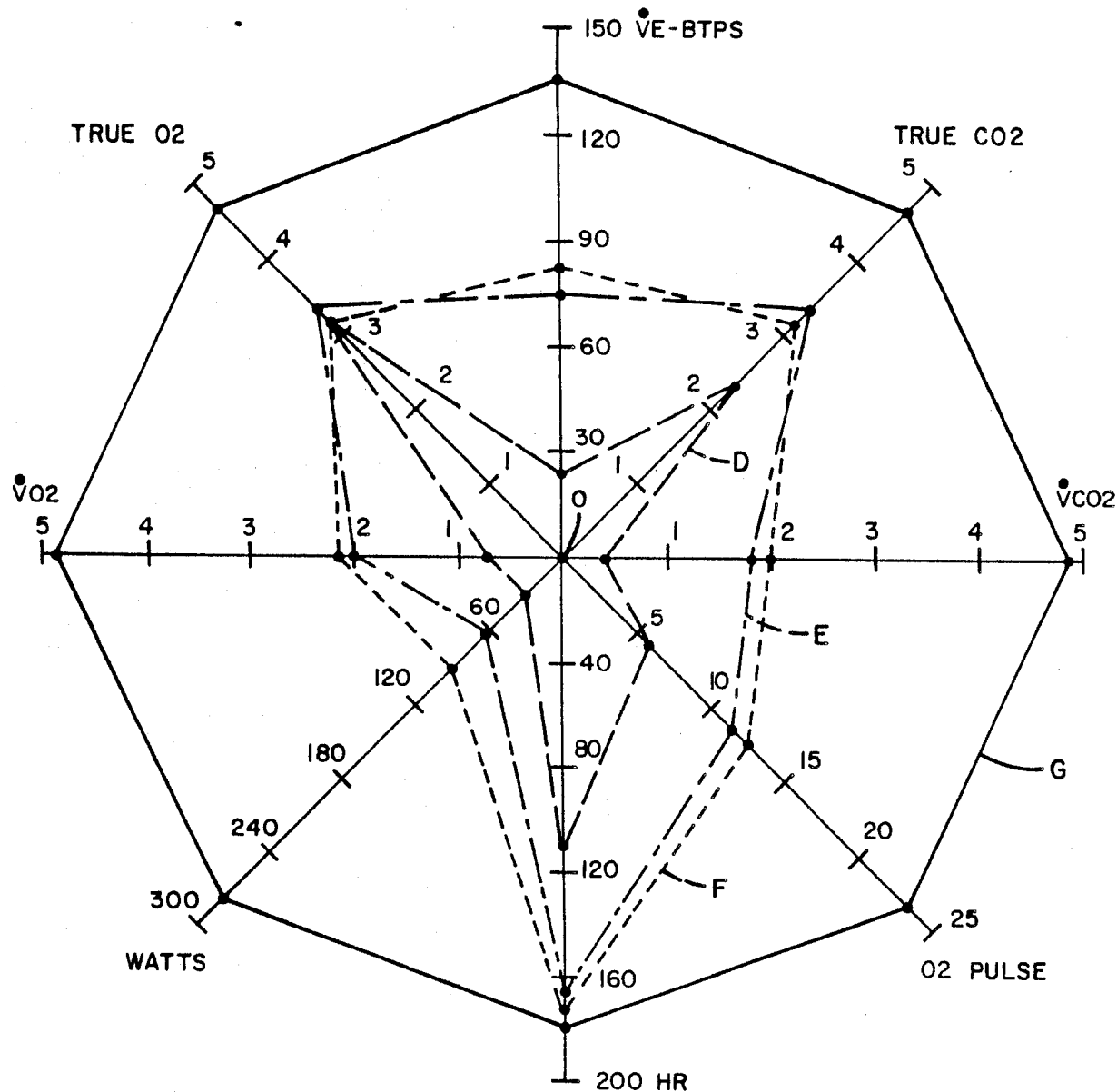

To better illustrate the advantage of the method of the present invention in recognizing abnormal cardiopulmonary function, reference is next made to the graph of FIG. 4 which represents the metabolic data obtained from a patient at three separate levels of work. The particular patient was a 21 year old female weighing 101 pounds and being 60.5 inches in height. This subject had earlier suffered a seizure while running which induced her to seek medical treatment and evaluation. Referring to the plotted data for this patient, the innermost irregular polygon identified by letter "D" and represented by a dashed line indicates the values of the various parameters for a very modest level of work. In fact, when exercising to the point at which about 30 Watts of energy are being expended which corresponds to a level of exercise attained in a very slow walk, the patient's heart rate rose to approximately 110 beats per minute. Irregular polygon "E" shows that when the level of exercise was increase to a 60 Watt output (corresponding to the energy required in walking at a normal pace), the patient's heart rate exceeded 160 beats per minute. The irregular polygon "F" results when straightline segments are drawn through points on adjacent axes corresponding to a level of work of approximately 90 Watts which is achieved when a normal subject is walking at slightly above a leisurely pace, a brisk pace requiring approximately 120 Watts of energy. Because the heart rate was becoming overly elevated for such modest level of work, the exercise testing was discontinued. Again, for ease of analysis, a regular polygon labeled "G" has been superimposed upon the graph of FIG. 4, its vertexes being disposed at normal or expected maximums for the various cardiopulmonary parameters being plotted. By comparing the irregular polygon "F" with the regular polygon "G", it becomes immediately apparent that the subject suffers from cardiopulmonary impairment.

It is currently postulated that specific shapes may be highly correlated to a type or class of cardiopulmonary diseases. For example, test to date show that a cardiac patient who has a high heart rate and relative low oxygen uptake and work rate during maximal exercise presents graphic data somewhat in the shape of a "shield". In addition, a graphic plot that looks like a "tent" may indicate that excessive ventilation is needed for a relatively low work rate, possibly characterizing a plumonary disease. The ultimate potential of the method of this invention has not, as yet, been fully realized. It does, however, include an overall graphic presentation of test results and the key factors currently encompassed in the interpretation of cardiopulmonary exercise tests.

The method of the present invention further contemplates the use of a clear plastic overlay having a regular polygon scribed or printed thereon, there being an overlay for males, another for females, and still others for persons of differing ages and, in this fashion, the actual measured data obtained by the cardiopulmonary exercise system can be compared to expected norms or maimums as reflected on those overlays.

The invention has been described herein in considerable detail, in order to comply with the Patent Statutes and to provide those skilled in the art with information needed to apply the novel principles and to carry out the inventive method. However, it is to be understood that the invention can be carried out in alternative ways, both as to the equipment employed and the operating procedures utilized and, hence, the scope of the invention should be determined by the accompanying claims.

What is claimed is:

1. A method for ascertaining the functional capacity of the cardio-respiratory system in the course of controlled exercise from measured cardio-respiratory data of living subjects by which key cardio-respiratory variables are readily located and distinctly displayed, comprising:
    (a) plotting a plurality of regularly spaced axes intersecting at a center point, each of said axes being associated with a different preselected cardio-respiratory variable obtained during incremental stress testing;
    (b) providing quantified scale markings on each of said axes at differing radial locations therealong, said scale markings being such that expected normal values of each of said variables will be generally an optimal distance from said center;
    (c) locating the magnitude of the actual measured values of said cardio-respiratory variables for given workloads with respect to such scale markings on appropriate ones of said plurality of axes;
    (d) constructing line segments from the points on said axes corresponding to said locations of the magnitude of actual measured values to that of an adjacent axis to form a closed polygon for each level of workload during the stress testing procedure; and
    (e) following the line segments extending through the maximum measured value on one of said plurality of axes to the corresponding measured value on another of said plurality of axes for the same level of workload to determine the subject's anaerobic threshold and the onset of respiratory compensation.

2. The method as in claim 1 wherein said data comprises numerical measurements from the group of cardiopulmonary function variables including $CO_2$ output, $O_2$ pulse, heart rate, work, $O_2$ uptake, true $O_2$, ventilatory equivalent, and true $CO_2$.

3. The method as in claim 2 wherein each individual cardiopulmonary function variable in said group is plotted on separate ones of said plurality of axes.

4. The method as in claim 2 wherein oxygen uptake $\dot{V}O_2$, is plotted on said another of said plurality of axes and true $O_2$ is plotted on said one of said plurality of axes.

5. The method as in claim 2 wherein oxygen uptake $\dot{V}O_2$, is plotted on said another of said plurality of axes and true $CO_2$ is plotted on said one of said plurality of axes.

* * * * *

UNITED STATES PATENT AND TRADEMARK OFFICE
CERTIFICATE OF CORRECTION

PATENT NO. : 4,930,519

DATED : June 5, 1990

INVENTOR(S) : Catherine A. Anderson, et al.

It is certified that error appears in the above-identified patent and that said Letters Patent is hereby corrected as shown below:

In column 6, line 66, before "data" insert -- cardio-respiratory --; in lines 66-67, delete "comprises" and insert -- comprise --.

Signed and Sealed this

Twenty-third Day of July, 1991

Attest:

HARRY F. MANBECK, JR.

Attesting Officer

Commissioner of Patents and Trademarks